United States Patent [19]

Fujimaki et al.

[11] Patent Number: 5,055,297
[45] Date of Patent: Oct. 8, 1991

[54] IMMUNOPOTENTIATOR

[75] Inventors: Michio Fujimaki; Shojiro Ikematsu; Masao Hada; Hidetaka Fukue, all of Tokyo; Katsuhiro Fukutake, Fujisawa, all of Japan

[73] Assignee: Tsumura Juntendo, Tokyo, Japan

[21] Appl. No.: 254,772

[22] PCT Filed: Feb. 25, 1988

[86] PCT No.: PCT/JP88/00199
§ 371 Date: Sep. 21, 1988
§ 102(e) Date: Sep. 21, 1988

[30] Foreign Application Priority Data

Mar. 27, 1987 [JP] Japan .................................. 62-73705
Mar. 27, 1987 [JP] Japan .................................. 62-73706

[51] Int. Cl.⁵ ............................................ A61K 35/78
[52] U.S. Cl. ................................. 424/195.1; 514/885
[58] Field of Search ...................... 424/195.1; 514/885

[56] References Cited

U.S. PATENT DOCUMENTS 4,469,685 9/1984 Kojima et al. .................. 424/195.1

FOREIGN PATENT DOCUMENTS 56-79623  6/1981 Japan .
56-118519 7/1982 Japan .
62-48619  3/1987 Japan .

OTHER PUBLICATIONS

Japanese Document Dated Jun. 10, 1982, pp. 25–27.

Primary Examiner—John W. Rollins
Attorney, Agent, or Firm—Burns, Doane, Swecker & Mathis

[57] ABSTRACT

An immunopotentiator for patients with viruses of an acquired immune deficiency syndrome, which contains Sho-saiko-to (Xiao-Chai-Hu-Tang) or Ninzin-to (Ren-Shen-Tang). Sho-saiko-to (Xiao-Chai-Hu-Tang) or Ninzin-to (Ren-Shen-Tang) according to the formulations of Chinese medicine, is used in situ or in the form of a preparation.

5 Claims, No Drawings

IMMUNOPOTENTIATOR

TECHNICAL FIELD

The present invention relates to an immunopotentiator for patients infected with viruses of an acquired immune deficiency syndrome.

BACKGROUND ART

The acquired immune deficiency syndrome (AIDS) is a disease which is caused by infection with viruses of an immune deficiency syndrome and characterized by a serious cellular immune deficiency. Because a radical cure has not been established for this disease, and further, the high mortality rate thereof, a serious social problem has developed.

At present, as a therapeutic agent for acquired immune deficiency syndrome, there are mentioned antivirus agents such as azide thymidine or the like, immune activators such as interleukin-2, interferon-$\gamma$ or the like, but these agents do not have decisive therapeutic effects, and therefore, the development of a therapeutic agent for the treatment of acquired immune deficiency syndrome is strongly desired.

DISCLOSURE OF THE INVENTION

The object of the present invention is to provide an immunopotentiator for patients with viruses of an acquired immune deficiency syndrome for the treatment of the acquired immune deficiency syndrome.

The present inventors have conducted research into the immune activating effect of a variety of formulations of Chinese medicines on patients infected with viruses of an acquired immune deficiency syndrome. As a result, the inventors found that Sho-saiko-to (Xiao-Chai-Hu-Tang), which is a formulation of Chinese medicine comprising Bupleuri Radix (root from the plant *Bulpeurum falcatum* Linne), Scutellariae Radix (root from the plant *Scutellaria baicalensis* Georgi, from which the periderm has been removed), Glycyrrhizae Radix (root and stolon of the plant *Glycyrrhiza uralensis* Fisher, *Glycyrrhiza glabra* Linne or other species of the Glycyrrhiza genus), Ginseng Radix (root from the plant *Panax ginseng* C. A. Mayer, from which rootlets have been removed, or which has been quickly passed through hot water), Zingiberis Rhizoma (rhizome from the plant *Zingiber officinale* Roscoe), Zizyphi Fructus (fruit from the plant *Zizphus jujuba* Miller var. inermis; Rehder or other allied plants) and Pinelliae Tuber (Tuber from the plant *Pinellia ternate* Breitenbach, from which the cork layer has been removed) and Ninzin-to (Ren-Shen-Tang), which is another formulation of a Chinese medicine comprising Glycyrrhizae Radix, Zingiberis Siccatum Rhizoma (dried rhizome from the plant *Zinber officinale* Roscoe), Atractylodis Rhizoma (rhizome from the plant *Atractylodes ovata* De Candolle or its varieties) and Ginseng Radix, have immune activating effects on patients with viruses of acquired immune deficiency syndrome. The present invention is based on this knowledge and is an immunopotentiator which contains Sho-saiko-to (Xiao-Chai-Hu-Tang) or Ninzin-to (Ren-Shen-Tang), for patients infected with acquired immune deficiency syndrome

BEST MODE FOR CARRYING OUT THE INVENTION

Sho-saiko-to (Xiao-Chai-Hu-Tang) is disclosed in the classic references of formulations of Chinese medicine as Shokanron (Shang-Han-Lun) and Kinkiyoryaku (Jin-Kui-Yao-Lue) in which the constituting crude drugs, amounts, extraction methods and the like thereof are described, and is applied to various diseases such as disorders of hepatic function, defect of recovery from post-parturition, or the like. Moreover, it has been already known in the art that it has an immune activating effect on patients with cancer or the like. Similarly, Ninzin-to (Ren-Shen-Tang) is also disclosed in the aforementioned classic references of formulations of Chinese medicine as Shokanron or Kinkiyoryaku, in which the constructing crude drugs, amounts, extraction methods and the like thereof are described, and is applied to various diseases such as acute or chronic enterogastric catarrh, gastroatonia, gastric dilation, hyperemesis, nephroscherosis and the like. However, it has not been hitherto known that Sho-saiko-to (Xiao-Chai-Hu-Tang) and Ninzin-to (Ren-Shen-Tang) have effects on activating the immune function of patients with acquired immune deficiency syndrome The term Sho-saiko-to (Xiao-Chai-Hu-Tang) used herein means any formulation which is prepared by incorporating the ratio of respective crude drugs in accordance with the description of the classic references such as Shokanron, Kinkiyoryaku or the like.

As an illustration of incorporating ratios of respective crude drugs of Sho-saiko-to (Xiao-Chai-Hu-Tang), there are preferably mentioned the ratios of 4–7 parts by weight of Bupleuri Radix, 3 parts by weight of Scutellariae Radix, 2 parts by weight of Glycyrrhizae Radix, 2–3 parts by weight of Ginseng Radix, 1 part by weight of Zingiberis Rhizoma, 2–3 parts by weight of Zizyphi Fructus and 4–5 parts by weight of Pinelliae Tuber.

Sho-saiko-to (Xiao-Chai-Hu-Tang) can be orally administered in three portions of an immunopotentiator which has been prepared, for example, by condensing the mixture of 7 g of Bupleuri Radix, 3 g of Scutellariae Radix, 3 g of Ginseng Radix, 1 g of Zingiberis Rhizoma, 3 g of Zizyphi Fructus, and 5 g of Pinelliae Tuber in 600 ml of water to a volume of 350 ml, removing the residue, and again condensing the liquid to a volume of 200 ml. However, in consideration of the administration ease and the transportation convenience, the dry extract powder or an extract preparation of the Chinese medicine also can be used as the immunopotentiator.

Particularly, Sho-saiko-to (Xiao-Chai-Hu-Tang), which is prepared by the following method, is preferred for producing the pharmacological effect thereof.

According to Shokanron and Kinkiyoryaku, to a mixture of 7 g of Bupleuri Radix, 3 g of Scutellariae Radix, 2 g of Glycyrrhizae Radix:, 3 g of Ginseng Radix, 1 g of Zingiberis Rhizoma, 3 g of Zizyphi Fructus, and 5 g of Pinelliae Tuber is added 10 to 12 times the amount of purified water, the extraction is carried out at 95° to 100° C. for about 60 minutes, and then the mixture is subjected to solid-liquid separation. The separated liquid thus, obtained is spray-dried to obtain an extract powders of Sho-saiko-to (containing, 4.5 g of the dry extract, 25.0 to 52.0 mg of glycyrrhizine, 90 to 210 mg of baicalein, and 2.3 to 6.9 mg of peychosaponin $b_z$).

For obtaining the preparation, appropriate vehicles, such as adminiculum or the like used for ordinary preparations, can be added to make preparations such as powder, granules, tablets, capsules or the like in the usual way.

The term Ninzin-to (Ren-Shen-Tang) used herein may mean any formulation which is prepared by incorporating ratio of respective crude drugs in accordance with the description of the classic references such as Shokanron, Kinkiyoryaku or the like.

Particularly, the Chinese medicine prepared in the constructing ratios of 3 parts by weight of Glycyrrhizae Radix, 3 parts by weight of Zingiberis Siccatum Rhizoma, 3 parts by weight of Atractylodis Rhizoma and 3 parts by weight of Ginseng Radix in accordance with Shokanron or Kinkiyoryaku is preferred from the viewpoint of the effect thereof.

Ninzin-to (Ren-Shen-Tang) can be administered in three portions of an immunopotentiator which has been prepared by condensing the mixture of 3 g of Glycyrrhizae Radix, 3 g of Zingiberis Siccatum Rhizoma, 3 g of Atractylodis Rhizoma, and 3 g of Ginseng Radix in 600 ml of water to a volume of 350 ml, removing the residue, and again condensing the liquid to a volume of 200 ml. However, in consideration of the administration ease and transportation convenience, the dry extract powder or an extract preparation of the Chinese medicine also can be used as the immunopotentiator.

For example, an extract which has been prepared by hot extraction of the mixture of 3 parts by weight of Glycyrrhizae Radix, 2-3 parts by weight of Zingiberis Siccatum Rhizoma, 3 parts by weight of Atractylodis Rhizoma, and 3 parts by weight of Ginseng Radix with 10 times the amount of water is filtered and dried to give an extract powder of Ninzin-to (Ren-Shen-Tang), to which appropriate vehicles, adminiculum or the like used for ordinary preparations can be added to make preparations such as powder, granules, tablets, capsules or the like in the usual way of manufacturing preparations.

Specific examples for preparing the immunopotentiator of the present invention are illustrated below.

SPECIFIC EXAMPLE 1

To a mixture of 7 g of Bupleuri Radix, 3 g of Scutellariae Radix, 2 g of Glycyrrhizae Radix, 3 g of Ginseng Radix, 1 g of Zingiberis Rhizoma, 3 g of Zizyphi Fructus, and 5 g of Pinelliae Tuber was added 300 ml of purified water, and the extraction was carried out at 100° C. for 60 minutes, the mixture centrifugalized after extraction and the separated liquid thus obtained spray-dried at 50° C. or less to obtain the extract powder of Sho-saiko-to (Xiao-Chai-Hu-Tang). When the components in 4.5 g of the dry extract were quantitatively determined, the values of 42.5 mg of glycyrrhizine, 160 mg of baicalein, and 4.5 mg of psychosaponin $b_z$ were obtained.

SPECIFIC EXAMPLE 2

To a mixture of crude drugs of 3 g of Glycyrrhizae Radix, 3 g of Zingiberis Siccatum Rhizoma, 3 g of Atractylodis Rhizoma, and 3 g of Ginseng Radix was added a ten-times amount, that is, 120 ml, of water, and the mixture was subjected to, extraction under heating. The thus obtained extract was filtered and then spray-dried to obtain 2.4 g of a dry extract powder.

Referring to the immune activating effect of the immunopotentiator of the present invention on patients with viruses of acquired immune deficiency syndrome, this is explained by the experimental examples below.

EXPERIMENTAL EXAMPLE 1

Hemophilia patients infected with viruses of acquired immune deficiency syndrome caused by blood transfusion were administered with a preparation of 4.5 g of the extract powder obtained in the abovementioned specific example 1, in three portions per day over a period of 3 months. Before dosage and 1, 2, 3, and 6 months after dosage, the number of leukocytes, lymphocytes, helper T cells (OKT4 positive cells), suppressor T cells (OKT8 positive cells), the ratio of OKT-4/OKT8 in blood, and the variations of the two-color analytical values were measured.

As a result, the ratio of OKT4/OKT8, which was 0.37 before dosage, increased to 0.55 6 months after dosage, and the number of OKT 8 positive cells decreased from 649/$\mu$l to 390/$\mu$l.

EXPERIMENTAL EXAMPLE 2

Five patients infected with viruses of acquired immune deficiency syndrome were administered 4.5 g of the extract powder obtained in the aforementioned Specific Example 1, in three portions per day for 3 months. Before dosage and 1, 2, and 3 months after dosage, the number of leukocytes, lymphocytes, helper T cells (OKT4), suppressor T cells (OKT8), the ratio of OKT4/OKT8, and the variations of the two-color analytical values were measured.

The results are shown in Table 1.

TABLE 1

| | |
|---|---|
| Increase of lymphocyte | 60% |
| Increase of OKT4 | 60% |
| Increase of OKT8 | 60% |
| Increase of the ratio of OKT4/OKT8 | 40% |
| Two-color analysis | |
| Rising of $CD4^+2H4^+$ | 80% |
| Rising of $CD4^+2H4^-$ | 20% |
| Rising of $CD8^+CD11^+$ | 80% |
| Rising of $CD8^+CD11^-$ | 40% |
| Rising of $CD8^+HLA\text{-}DR^+$ | 60% |
| Rising of $Leu7^-CD16^+$ | 40% |
| Rising of $Leu7^+CD16^+$ | 60% |

EXPERIMENTAL EXAMPLE 3

Four patients infected with viruses of acquired immune deficiency syndrome were administered 2.5 g of the extract powder obtained in the aforementioned Specific Example 2, in three portions per day for 3 months. Before dosage and 1, 2, and 3 months after dosage, the number of leukocytes, lymphocytes, helper T cells (OKT4), suppressor T cells (OKT8), the ratio of OKT4/OKT8, and the variations of the two-color analytical values were measured.

The results are shown in Table 2.

TABLE 2

| | |
|---|---|
| Increase of lymphocyte | 75% |
| Increase of OKT4 | 50% |
| Increase of OKT8 | 50% |
| Increase of the ratio of OKT4/OKT8 | 25% |
| Two-color analysis | |
| Rising of $CD4^+2H4^+$ | 100% |
| Rising of $CD4^+2H4^-$ | 50% |
| Rising of $CD8^+CD11^+$ | 75% |
| Rising of $CD8^+CD11^-$ | 50% |
| Rising of $CD8^+HLA\text{-}DR^+$ | 100% |
| Rising of $Leu7^-CD16^+$ | 75% |
| Rising of $Leu7^+CD16^+$ | 50% |

From the above results, it was confirmed that the immunopotentiator of the present invention has an immune activating effect on patients infected with viruses of acquired immune deficiency syndrome.

Next, when the acute toxicity of the immunopotentiator of the present invention upon oral dosage was evaluated with ddY male mice and Wister male rats, no animal died even at an oral dosage of 15 g/kg (dosage limit) of the immunopotentiator of the present invention obtained in Specific Example 1. Thus, the immunopotentiator of the present invention has extremely low toxicity and high safety. Moreover, Sho-saiko-to (Xiao-Chai-Hu-Tang) and Ninzin-to (Ren-Shen-Tang) have been clinically used from ancient times as Chinese medicines, and it has been confirmed that these medicines have few side-effects. As shown by the experimental data and results of the acute toxicity tests of the present invention, the effective dose of the immunopotentiator of the present invention differs depending on the age, body weight and degree of the disease of the patients, and an ordinary oral dose for adult patients is preferably in the range of 1–10 g per day, and should be administered three times per day depending on the symptoms.

The present invention is specifically explained by reference to examples but is not limited thereto.

EXAMPLE 1

A 200 g portion of the dry extract powder prepared in the aforementioned specific example 1 was mixed with 89 g of lactose and 1 g of magnesium stearate, and the mixture was subjected to a pressing operation in a single type tablet making machine to make slug tablets having a diameter of 20 mm and a weight of ca. 2.3 g. The slug tablets were ground with an oscillator and passed through a screen to give preferred granules of 20–50 meshes.

These granules are administered 3 times per day in an unit dose of 0.5–4.5 g (corresponding to 0.34–3.10 g of the weight of the dry extract powder of the immunopotentiator of the present invention), depending on the symptoms.

EXAMPLE 2

A 200 g portion of the dry extract powder prepared in the aforementioned specific example 1 was mixed with 20 g of fine crystalline cellulose and 5 g of magnesium stearate, and the mixture was subjected to a pressing operation in a single type tablet making machine to prepare tablets having a diameter of 7 mm and a weight of 225 mg. One tablet contained 200 mg of the dry extract powder of the immunopotentiator of the present invention. The tablet was administered in a dose of 2–10 tablets, 3 times per day.

EXAMPLE 3

The dry extract powder prepared in the aforementioned specific example 1 was charged in an amount of 500 mg in a hard capsule. The capsule was given three times per day, at a dosage of 2–20 capsules depending on the symptoms.

EXAMPLE 4

A 200 g portion of the dry extract powder prepared in the aforementioned specific example 1 was mixed with 89 g of lactose and 1 g of magnesium stearate, and the mixture was subjected to a pressing operation in a single type tablet making machine to make slug tablets having a diameter of 20 mm and a weight of ca. 2.3 g. The slug tablets were ground with an oscillator and passed through a screen to give preferred granules of 20–50 meshes.

These granules are administered 3 times per day in an unit dose of 0.5–4.5 g (corresponding to 0.34–3.10 g of the weight of dry extract powder of the immunopotentiator of the present invention) depending on the symptoms.

EXAMPLE 5

A 200 g portion of the dry extract powder prepared in the aforementioned specific example 2 was mixed with 20 g of fine crystalline cellulose and 5 g of magnesium stearate, and the mixture was subjected to a pressing operation in a single type tablet making machine to prepare tablets having a diameter of 7 mm and a weight of 225 mg. One tablet contained 200 mg of the dry extract powder of the immunopotentiator of the present invention. The tablet was administered in a dose of 2–10 tablets, 3 times per day.

EXAMPLE 6

The dry extract powder prepared in the aforementioned specific example 2 was charged in an amount of 500 mg in a hard capsule. The capsule was given three times per day at a dosage of 2–20 capsules, depending on the symptoms.

We claim:

1. A method for treating a patient infected with a virus causing acquired immune deficiency syndrome, said method comprising administering a therapeutically effective amount of an immunopotentiator to treat said acquired immune deficiency syndrome, said immunopotentiator comprising Sho-saiko-to (Xiao-Chai-Hu-Tang) or Ninzin-to (Ren-Shen-Tang).

2. A method according to claim 1, wherein said Sho-saiko-to (Xiao-Chai-Hu-Tang) comprises Bupleuri Radix, Scutellariae Radix, Glycyrrhizae Radix, Ginseng Radix, Zingiberis Rhizoma, Zizyphi Fructus and Pinelliae Tuber.

3. A method according to claim 2, wherein said Sho-saiko-to (Xiao-Chai-Hu-Tang) comprises between 4 to 7 parts by weight of Bupleuri Radix, 3 parts by weight of Scutellariae Radix, 2 parts by weight of Glycrrhizae Radix, between 2 to 3 parts by weight of Ginseng Radix, 1 part by weight of Zingiberis Rhizoma, between 2 to 3 parts by weight of Zizyphi Fructus and between 4 to 5 parts by weight of Pinelliae Tuber.

4. A method according to claim 1, wherein said Ninzin-to (Ren-Shen-Tang) comprises Glycyrrihizae Radix, Zingiberis Siccatum Rhizoma, Atradctylodis Rhizoma and Ginseng Radix.

5. A method according to claim 4, wherein said Ninzin-to (Ren-Shen-Tang) comprises 3 parts by weight of Glycyrrhizae Radix, 3 parts by weight of Zingiberis Siccatum Rhizoma, 3 parts by weight of Atractylodis Rhizoma and 3 parts by weight of Ginseng Radix.

* * * * *